United States Patent
Hebert

(10) Patent No.: US 10,806,368 B2
(45) Date of Patent: Oct. 20, 2020

(54) MOTION MANAGEMENT IN MRI-GUIDED LINAC

(71) Applicant: Elekta, Inc., Atlanta, GA (US)

(72) Inventor: Francois Paul George Rene Hebert, Montreal (CA)

(73) Assignee: Elekta, Inc., Atlanta, GA (US)

( * ) Notice: Subject to any disclaimer, the term of this patent is extended or adjusted under 35 U.S.C. 154(b) by 673 days.

(21) Appl. No.: 15/533,228

(22) PCT Filed: Dec. 7, 2015

(86) PCT No.: PCT/US2015/064229
§ 371 (c)(1),
(2) Date: Jun. 5, 2017

(87) PCT Pub. No.: WO2016/094284
PCT Pub. Date: Jun. 16, 2016

(65) Prior Publication Data
US 2017/0360325 A1    Dec. 21, 2017

Related U.S. Application Data

(60) Provisional application No. 62/090,601, filed on Dec. 11, 2014.

(51) Int. Cl.
*A61B 5/055* (2006.01)
*A61N 5/10* (2006.01)
(Continued)

(52) U.S. Cl.
CPC .......... *A61B 5/055* (2013.01); *A61B 5/0036* (2018.08); *A61B 5/4836* (2013.01); *A61N 5/107* (2013.01);
(Continued)

(58) Field of Classification Search
CPC .......... G01R 33/4808; G01R 33/56509; G01R 33/5676; A61B 5/4836; A61B 5/055;
(Continued)

(56) References Cited

U.S. PATENT DOCUMENTS 5,553,618 A * 9/1996 Suzuki ............. A61N 7/02
600/411
2003/0048267 A1  3/2003 Allouche
(Continued)

FOREIGN PATENT DOCUMENTS

| AU | 2015360825 | 5/2018 |
|----|------------|--------|
| CN | 101404924  | 4/2009 |

(Continued)

OTHER PUBLICATIONS

"Australian Application Serial No. 2015360825, Response filed Jan. 24, 2018 to First Examiners Report dated Oct. 5, 2017", 16 pgs.
(Continued)

*Primary Examiner* — Bo Joseph Peng
(74) *Attorney, Agent, or Firm* — Schwegman Lundberg & Woessner, P.A.; Sanjay Agrawal

(57) ABSTRACT

Described herein is a system and method of controlling real-time image-guided adaptive radiation treatment of at least a portion of a region of a patient. The computer-implemented method comprises obtaining a plurality of real-time image data corresponding to 2-dimensional (2D) magnetic resonance imaging (MRI) images including at least a portion of the region, performing 2D motion field estimation on the plurality of image data, approximating a 3-dimensional (3D) motion field estimation, including applying a conversion model to the 2D motion field estimation, determining at least one real-time change of at least a portion of the region based on the approximated 3D motion field estimation, and controlling the treatment of at least a (Continued)

portion of the region using the determined at least one change.

27 Claims, 5 Drawing Sheets

(51) Int. Cl.
    *G01R 33/48*         (2006.01)
    *A61B 5/00*         (2006.01)
    *G06T 7/269*         (2017.01)
    *G06T 7/207*         (2017.01)
    *G01R 33/565*         (2006.01)
    *G01R 33/567*         (2006.01)

(52) U.S. Cl.
    CPC .......... *A61N 5/1049* (2013.01); *A61N 5/1067* (2013.01); *A61N 5/1068* (2013.01); *G01R 33/4808* (2013.01); *G06T 7/207* (2017.01); *G06T 7/269* (2017.01); *A61N 2005/1055* (2013.01); *G01R 33/5676* (2013.01); *G01R 33/56509* (2013.01); *G06T 2207/10088* (2013.01); *G06T 2207/20048* (2013.01)

(58) Field of Classification Search
    CPC .................... G06T 7/269; G06T 7/207; G06T 2207/10088; G06T 2207/20048; A61N 5/1067; A61N 5/1068; A61N 5/107; A61N 5/1049; A61N 2005/1055
    See application file for complete search history.

(56) References Cited

U.S. PATENT DOCUMENTS

| | | | |
|---|---|---|---|
| 2006/0074292 | A1 | 4/2006 | Thomson et al. |
| 2009/0052757 | A1 | 2/2009 | Khamene et al. |
| 2011/0092793 | A1 | 4/2011 | Thomson et al. |
| 2012/0245453 | A1 | 9/2012 | Tryggestad et al. |
| 2013/0035588 | A1* | 2/2013 | Shea .................. G01R 33/4833 600/413 |
| 2014/0355855 | A1 | 12/2014 | Miao et al. |

FOREIGN PATENT DOCUMENTS

| | | |
|---|---|---|
| CN | 102274039 | 12/2011 |
| CN | 102982582 | 3/2013 |
| CN | 107206252 | 9/2017 |
| JP | 2003135428 | 5/2003 |
| RU | 2007132466 | 3/2009 |
| WO | WO-2016094284 A1 | 6/2016 |
| WO | WO-2016094284 A9 | 6/2016 |

OTHER PUBLICATIONS

"Russian Application Serial No. 2017123803, Response filed Oct. 12, 2018 to Office Action dated Aug. 14, 2018", w English claims.
"Chinese Application Serial No. 201580074676.8, Office Action dated Apr. 22, 2019", w English translation, 14 pgs.
"Chinese Application Serial No. 201580074676.8, Response filed Sep. 5, 2019 to Office Action dated Apr. 22, 2019", w English claims, 3 pgs.
"Japanese Application Serial No. 2017-531532, Notification of Reasons for Refusal dated Oct. 15, 2019", W English Translation, 7 pgs.
"Australian Application Serial No. 2018201316, First Examination Report dated Jun. 19, 2018", 4 pgs.
"Russian Application Serial No. 2017123803, Response filed Jul. 24, 2018 to Office Action dated May 28, 2018", w English Claims, 21 pgs.
"Russian Application Serial No. 2017123803, Office Action dated Aug. 14, 2018", W English Translation, 9 pgs.
"International Application Serial No. PCT/US2015/064229, International Preliminary Report on Patentability dated Jun. 22, 2017", 9 pgs.
"Australian Application Serial No. 2015360825, First Examiners Report dated Oct. 5, 2017", 4 pgs.
"Russian Application Serial No. 2017123803, Office Action dated May 28, 2018", w English Translation, 13 pgs.
"Australian Application Serial No. 2018201316, Response filed Jul. 26, 2018 to First Examination Report dated Jun. 19, 2018", 13 pgs.
"International Application Serial No. PCT/US2015/064229, International Search Report dated Mar. 2, 2016", 4 pgs.
"International Application Serial No. PCT/US2015/064229, Written Opinion dated Mar. 2, 2016", 7 pgs.
Alexander, D. C., et al., "Spatial Transformations of Diffusion Tensor Magnetic Resonance Images", IEEE Transactions on Medical Imaging, vol. 20, No. 11, (Nov. 2001), 1131-1139.
Chou, Chen-Rui, et al., "2D / 3D image registration using regression learning", Computer Vision and Image Understanding 117, (2013), 1095-1106.
Chou, Chen-Rui, et al., "Claret: A Fast Deformable Registration Method Applied to Lung Radiation Therapy", Fourth International (MICCAI) Workshop on Pulmonary Image Analysis, (2011), 113-124.
Davison, Andrew J., "Active Search for Real-Time Vision", In Proceedings of the IEEE International Conference on Computer Vision, [Online]. Retrieved from the Internet: <URL: http://pdf.aminer.org/000/293/002/active_search_for_real_time_vision.pdf>, (2005), 1-8.
De Senneville, Baudouin Denis, et al., "MR-Guided Thermotherapy of Abdominal Organs Using a Robust PCA-Based Motion Descriptor", IEEE Transactions on Medical Imaging, vol. 30, No. 11, (Nov. 2011), 1987-1995.
Dellaert, Frank, et al., "Fast Image-Based Tracking by Selective Pixel Integration", [Online]. Retrieved from the Internet: <URL: http://www.ius.cs.cmu.edu/IUS/saradar/Frank/framerate/framerate.html, (1999), 1-22.
He, Tiancheng, et el., "Estimating Dynamic Lung Images from High-Dimension Chest Surface Motion Using 4D Statistical Model", Medical Image Computing and Computer-Assisted Intervention—MICCAI 2014, Lecture Notes in Computer Science, vol. 8674, (2014), 138-145.
Klinder, Tobias, et al., "Prediction Framework for Statistical Respiratory Motion Modeling", Medical Image Computing and Computer-Assisted Intervention—MICCAI 2010, Lecture Notes in Computer Science vol. 6363, (2010), 327-334.
Peressutti, D., et al., "A Framework for Automatic Model-Driven 2D Echocardiography Acquisition for Robust Respiratory Motion Estimation in Image-Guided Cardiac Intervention", 2013 IEEE 10th International Symposium on Biomedical Imaging: From Nano to Macro, (Apr. 2013), 4 pgs.
Preiswerk, Frank, et al., "A Bayesian Framework for Estimating Respiratory Liver Motion from Sparse Measurements", Abdominal Imaging. Computational and Clinical Applications, Lecture Notes in Computer Science vol. 7029, (2012), 207-214.
Preiswerk, Frank, et al., "Robust Tumour Tracking From 2D Imaging Using a Population-Based Statistical Motion Model", Mathematical Methods in Biomedical Image Analysis (MMBIA), 2012 IEEE Workshop, (2012), 209-214.
Steininger, Philipp, et al., "A novel class of machine-learning-driven real-time 2D / 3D tracking methods: texture model registration (TMR)", Proc. of SPIE, vol. 7964, (2011), 79640G-1-9.
Xu, Yuan, et al., "A method for real-time volumetric imaging in radiotherapy using single x-ray projection", arXiv:1407.0667 [physics.med-ph], [Online]. Retrieved from the Internet: <URL: http://arxiv-web3.library.cornell.edu/abs/1407.0667>, (Jul. 2, 2014), 1-20.
Zhang, Qinghui, et al., "A Pattient-Specific Respiratory Model of Anatomical Motion for Radiation treatment Planning", Med. Phys. 34, (2007), 4772-4781.
"European Application Serial No. 15816333.7, Response filed Mar. 12, 2018 to Communication pursuant to Rules 161(1) and 162 EPC dated Sep. 8, 2017", 31 pgs.

(56) References Cited

OTHER PUBLICATIONS

"Japanese Application Serial No. 2017-531532, Response filed Dec. 16, 2019 to Notification of Reasons for Refusal dated Oct. 15, 2019", w/ English claims, 19 pgs.

* cited by examiner

MOTION MANAGEMENT IN MRI-GUIDED LINAC

CLAIM OF PRIORITY

This application is a U.S. national stage application filed under 35 U.S.C. § 371 from International Application Ser. No. PCT/US/2015/064229, filed on Dec. 7, 2015 and published as WO 2016/094284 on Jun. 16, 2016, which claims the benefit of priority of U.S. Provisional Patent Application Ser. No. 62/090,601, titled "MOTION MANAGEMENT IN MRI-GUIDED LINAC" to Francois Hebert, and filed on Dec. 11, 2014, which applications and publication are herein incorporated by reference in their entirety.

TECHNICAL FIELD

This disclosure relates to medical systems and, more particularly, to magnetic resonance or other imaging or radiotherapy treatment systems.

BACKGROUND

Radiation therapy (also referred to as radiotherapy) may be used in the treatment of cancer or other pathologies. A linear accelerator ("Linac") may be used in radiotherapy to direct a radiation beam to a desired location on a patient. The Linac may direct photons (e.g., as an X-ray), electrons, or other subatomic particles toward a target, such as a cancerous tumor. The radiation beam may be shaped to match a shape of the tumor, such as by using a multileaf collimator (e.g., which may include multiple tungsten leaves that may move independently of one another to create one or more specified radiation beam shapes).

Because healthy cells may be harmed or killed during radiotherapy treatment of a specified target, it may be desirable to minimize radiation to healthy tissue. Medical imaging may aid in this pursuit. Imaging systems such as computed tomography (CT), fluoroscopy, and magnetic resonance imaging ("MRI" or "MR imaging") may be used to determine the location of (localize) or track a target. An example of a radiotherapy treatment system integrated with an imaging system may include an MRI-Linac system (such as can be used for MRI-guided radiotherapy), which may be configured to use three-dimensional (3D) images of a target, such as a tumor, in radiotherapy to provide radiation to the target while reducing or minimizing radiation to other tissue.

The MRI-Linac system may include an accelerator, such as may be configured to rotate on a ring gantry around an MRI system. The patient to be treated may be positioned on a surface (e.g., a table, a bed, or a couch), such as may be centered inside the MRI-Linac system. MRI can provide a spatial map of hydrogen nuclei in tissues of the patient, and images may be acquired in a two-dimensional (2D) plane or 3D volume. Health care providers, such as oncologists, may prefer MRI-Linac imaging techniques because MRI may provide excellent soft tissue contrast without using ionizing radiation.

In an MRI-guided LINAC, for example, it can be desirable to localize the target position of the target and organs at risk (OARs) during the treatment itself. This can enable gating or tracking strategies to compensate for motion while the beam is on. In some modes of operation, this can be accomplished by the acquisition of sequential 2D MRI slices, for example alternating axial, coronal and sagittal slices. These 2D slices can be used to directly infer 3D target motion using direct segmentation or registration techniques.

These approaches may have the following limitations: 1) there can be significant out-of-plane motion, which can be difficult to localize with 2D slices; 2) slices are generally centered on the target, rendering it difficult to simultaneously track OARs; and 3) only information in the 2D slices is gathered during treatment, which makes it difficult to perform dose calculations, e.g., offline retrospective calculation of dosimetry for adaptive radiotherapy (dose compensation utilizes full 3D information of the patient's anatomy over time).

Overview

MR imaging can be performed in "real-time" (e.g., "online," "ongoing," or "continuously") during radiotherapy, such as to provide target location and motion information, e.g., 3D deformation and/or 3D rotation, for the radiation beam delivery. A target to be tracked can include an organ, such as a prostate, or a tumor relating to all or part of the organ. In image processing, one way in which a target can be determined to be in motion is if the location of the target changes relative to its background in the image. Image processing techniques to localize, track, or predict a location of a target can include image subtraction, such as can include using one or more absolute differences, or using edge, corner, or region of interest (ROI) image feature detection.

Fast and accurate 3D localization and tracking of the target can be important during radiotherapy, such as to account for patient motion (e.g., organ motion and/or tumor motion). Motion of a target, e.g., 3D deformation and/or 3D rotation, can be caused by one or more sources, such as patient respiration (e.g., a breathing cycle), a reflex (e.g., a cough, passing gas, etc.), intentional or unintentional patient movement, or other expected or unexpected target motion.

This disclosure describes techniques that can estimate 3D motion from a series of 2D MRI slices. As described in detail below, these techniques can include two main stages: 1) a learning stage where a conversion model is built that links 2D slices to the 3D motion; and 2) a tracking stage where 3D real-time tracking is performed based on the conversion model built in the learning stage. These techniques can estimate full 3D motion from 2D slices to provide the current change, e.g., one or more of 3D location, 3D deformation, and/or 3D rotation, of the target in real-time.

In an example, this disclosure is directed to a computer-implemented method of controlling real-time image-guided adaptive radiation treatment of at least a portion of a region of a patient. The computer-implemented method comprises obtaining a plurality of real-time image data corresponding to 2-dimensional (2D) magnetic resonance imaging (MRI) images including at least a portion of the region, performing 2D motion field estimation on the plurality of image data, approximating a 3-dimensional (3D) motion field estimation, including applying a conversion model to the 2D motion field estimation, determining at least one real-time change of at least a portion of the region based on the approximated 3D motion field estimation, and controlling the treatment of at least a portion of the region using the determined at least one change.

In an example, this disclosure is directed to a system for controlling real-time image-guided adaptive radiation treatment of at least a portion of a region of a patient. The system comprises a treatment adaptation system and a therapy controller circuit. The treatment adaptation system is configured to obtain a plurality of real-time image data corresponding to 2-dimensional (2D) magnetic resonance imaging (MRI) images including at least a portion of the region, perform 2D motion field estimation on the plurality of image data, approximate a 3-dimensional (3D) motion field estimation, including applying a conversion model to the 2D motion field estimation, and determine at least one real-time change of at least a portion of the region based on the approximated 3D motion field estimation. The therapy controller circuit is configured to control the treatment of at least a portion of the region using the determined at least one change.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments discussed in the present document. Such embodiments are demonstrative and not intended to be exhaustive or exclusive embodiments of the present apparatuses, systems, or methods.

DETAILED DESCRIPTION

Figure 1:
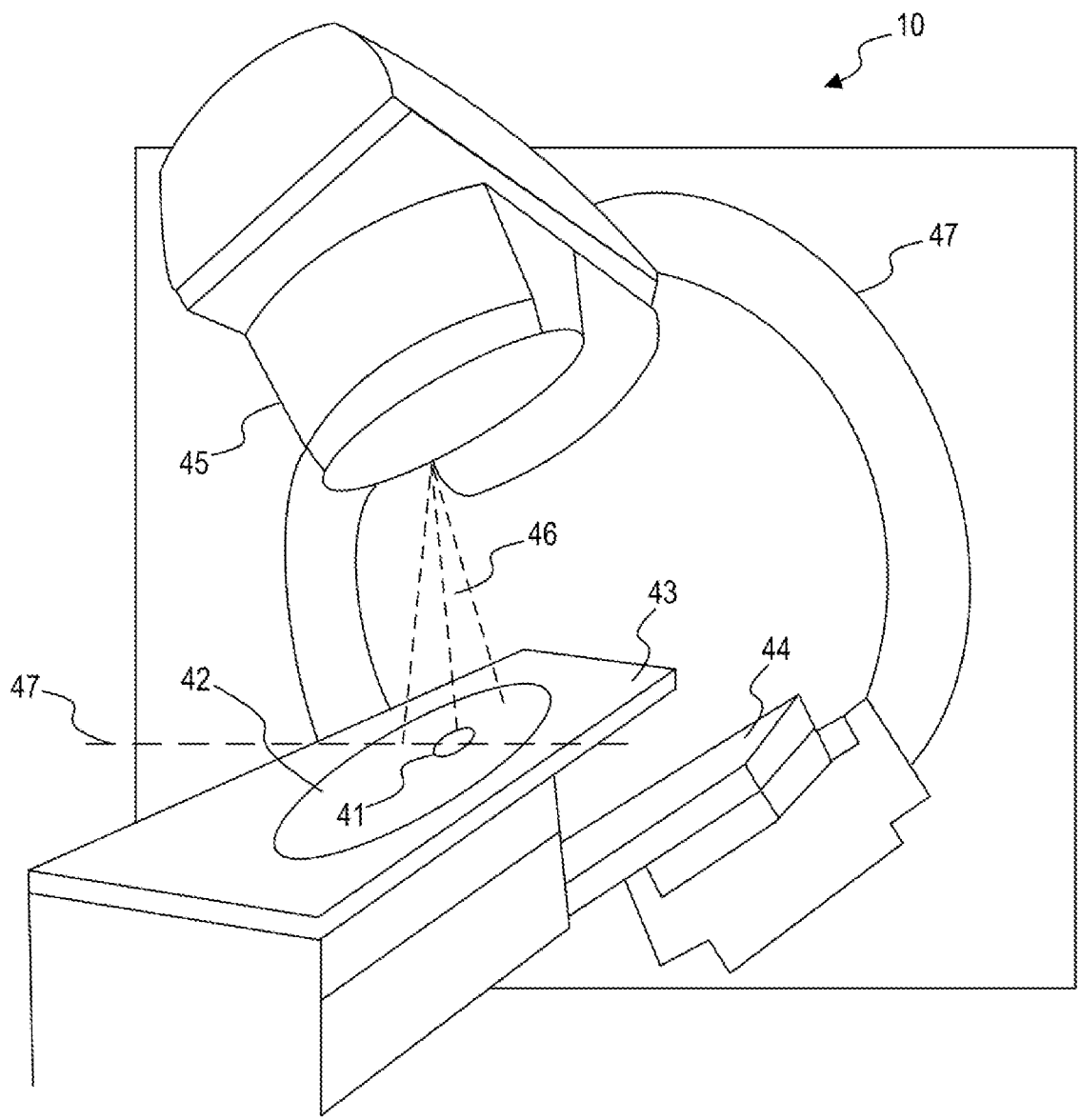
FIG. 1 is an example of a radiotherapy device that can be used to implement various techniques of this disclosure.

FIG. 1A illustrates an example of a radiotherapy device, e.g., a linear accelerator 10, according to some embodiments of the present disclosure. Using a linear accelerator 10, a patient 42 may be positioned on a patient table 43 to receive the radiation dose determined by the treatment plan. The linear accelerator 10 may include a radiation head 45 that generates a radiation beam 46. The entire radiation head 45 may be rotatable, such as around a horizontal axis 47. In an example, below the patient table 43 there may be provided a flat panel scintillator detector 44, which may rotate synchronously with radiation head 45, such as around an isocenter 41. The intersection of the axis 47 with the center of the beam 46, produced by the radiation head 45, can be referred to as the "isocenter." The patient table 43 may be motorized so that the patient 42 can be positioned with the tumor site at or close to the isocenter 41. The radiation head 45 may rotate about a gantry 47, such as to provide patient 42 with a plurality of varying dosages of radiation, such as according to the treatment plan.

Figure 1B:
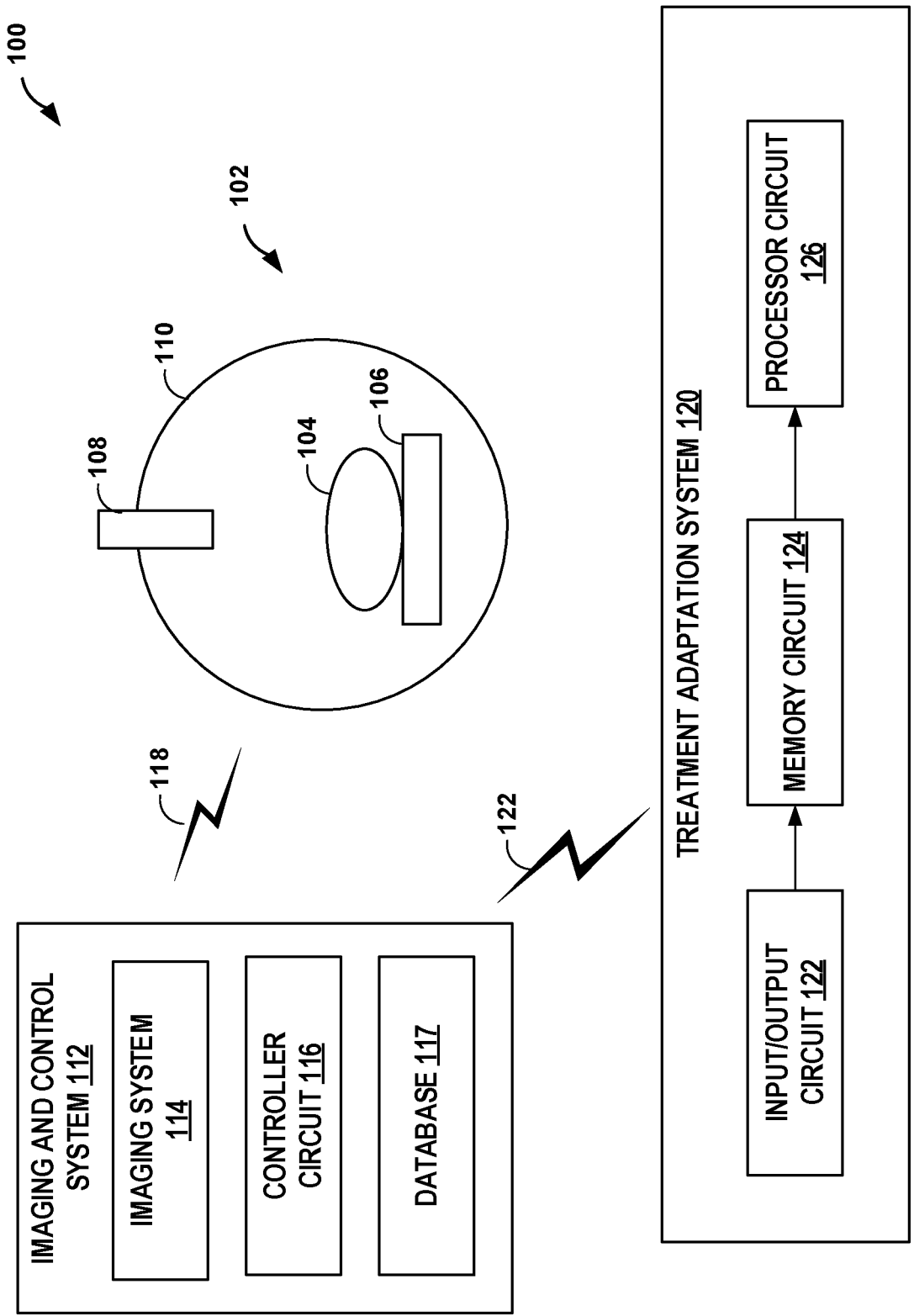
FIG. 1B is an example of portions of a system that can be used to provide real-time image guidance in accordance with various techniques of this disclosure.

FIG. 1B is an example of portions of an imaging or radiotherapy system 100, e.g., MRI-guided LINAC, that can be used to provide real-time image guidance in accordance with various techniques of this disclosure. More particularly, the system 100 of FIG. 1B can use images obtained in real-time to control or adapt a radiation therapy treatment plan in real-time. The system 100 can include a treatment apparatus 102 (e.g., a radiotherapeutic apparatus, such as can include a linear accelerator ("Linac")).

The patient 104 can be positioned on a patient support 106, such as a table, a couch, or other surface. The patient support 106 can be configured to change position such as relative to one or more other components of the treatment apparatus 102, such as to elevate or change the longitudinal position of the patient 104. Radiation can be emitted from a therapeutic radiation source 108 (e.g., accelerated particles such as x-rays or protons) toward the patient 104. In an example, the radiation source 108 can be configured to move, such as to rotate around the patient 104, such as by using a rotational support 110 (e.g., gantry) to which the therapeutic radiation source 108 can be attached. The therapeutic radiation source 108 can be configured to move, such as to rotate, such as by using a member or a mechanical arm, which can be connected to the treatment apparatus 102 and the therapeutic radiation source 108. The treatment apparatus 102 in an embodiment may be a linear accelerator "Linac" (e.g., as shown and described with respect to FIG. 1A) that can be configured to direct an x-ray beam toward a target (e.g., a cancer tumor) of the patient 104.

In addition, the system 102 can include an imaging and control system 112 (e.g., a magnetic resonance imaging (MRI) machine) that includes an imaging system 114 and a therapy controller circuit 116 (also referred to in this disclosure as "controller circuit 116" or "controller 116") in communication with the treatment apparatus 102, as depicted by lightning bolt 118 (e.g., lightning bolt 118 may be a wired or wireless connection). The imaging and control system 112 can also include a database 117, for example, to store acquired images. The imaging system 114 can include a magnetic resonance imaging (MRI) machine that can be used in combination with the treatment apparatus 102 (e.g., such as to provide an MRI linear accelerator ("MRI-Linac"). The MRI apparatus can be used to provide imaging information that can be used to control or adapt treatment of the patient 104. One or more other imaging systems can additionally or alternatively be included in or used with the system 102 or the imaging system 114, such as a computed tomography (CT) system.

The imaging system 114 can acquire, for example, three-dimensional (3D) images of the patient. For example, during a treatment planning phase, a health care worker, e.g., physician, nurse, physicist, or technician, can control the system 102 to acquire 3D planning image data prior to treatment of the patient, e.g., via the imaging system 114. The 3D planning image data can be useful in determining a precise location of a region of interest of the patient, e.g., a target. As another example, immediately prior to treatment, e.g., several days after the 3D planning image was acquired, the health care worker can control the system 102 to acquire a new 3D image that can be used to during the treatment. In addition, during the treatment of the patient 104, the imaging system 114 can acquire a plurality of 1-dimensional (1D) lines or 2-dimensional (2D) slices or 3D volume of MRI images including at least a portion of the region (which when combined could form a 3D image of the region).

The controller 116 can control one or more aspects of the system 102. For example, the controller 116 can control the position of the patient, e.g., via the patient support 106, control the radiation dosage emitted from the radiation source 108, control or adapt a beam aperture shape to track the target, and/or control the movement and/or positioning of the radiation source 108.

As described above, an MRI-Linac system can have its own controller circuit 116 to control both the imaging and Linac. However, in example implementations in which the imaging system 114 is a CT system, the controller of the CT system may not control the Linac. As such, separate controllers control a CT system and the Linac.

The system 102 can include a treatment adaptation system (TAS) 120 in communication with the imaging and control system 112, as depicted by lightning bolt 122. The TAS 120 can receive a previously obtained 3D image data volume, e.g., from MRI or CT scans, that corresponds to the 3D image acquired by the imaging system 114. The TAS can include an input/output circuit 122 for receiving and transmitting data, a memory circuit 124 for buffering and/or storing data, and a processor circuit 126. The memory circuit 124, which may be any suitably organized data storage facility can receive image data from the imaging and control system 112. The memory circuit 124 may receive the image data via a wireless or wired connection, through conventional data ports and may also include circuitry for receiving analog image data and analog-to-digital conversion circuitry for digitizing the image data. The memory circuit 124 can provide the image data to the processor circuit 126, which can implement the functionality of the present invention in hardware or software, or a combination of both on a general-purpose computer. In an embodiment, the processor circuit 126 may be a graphical processing unit (GPU).

As described in more detail below and in accordance with this disclosure, the TAS 120 can estimate 3D motion from a series of 2D slices acquired in real-time, e.g., using an MRI, to adapt a radiation therapy treatment plan in real-time. In a learning stage, the TAS 120 can build a conversion model that links 2D slices to previously obtained 3D image data volumes, e.g., acquired using MRI or CT. In a tracking stage, the TAS 120 can perform 3D real-time tracking based on the conversion model built in the learning stage. The TAS 120 can determine whether a region, e.g., a target, has changed position, and then output information to the imaging and control system 112 that can allow the therapy controller circuit 116 to control the therapy in response to a determined change in position.

Figure 2:
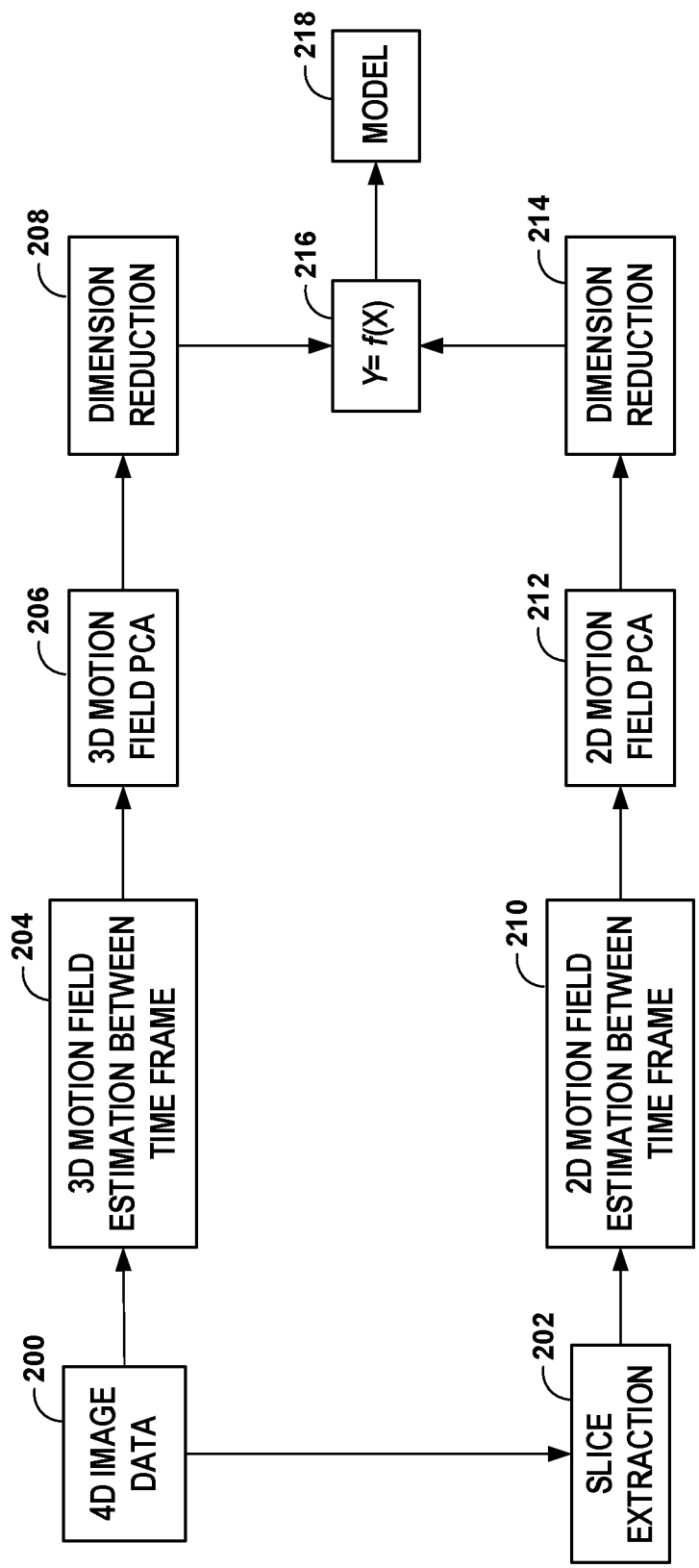
FIG. 2 is a flow diagram illustrating an example of a technique that can be used to build a conversion model that can link 2D slices to previously obtained 3D image data volumes.

FIG. 2 is a flow diagram illustrating an example of a technique that can be used to build a conversion model that can link 2D slices to previously obtained 3D image data volumes. The flow diagram of FIG. 2 can represent the learning stage in which the TAS 120 can build the conversion model that can link 2D slices to 3D motion. First, the TAS 120 can obtain a set of acquired 4D image data (block 200) from the imaging and control system 112. The image data can be acquired using MR or CT imaging techniques. The 4D image data includes 3D image data volumes obtained over a period of time. Optionally, the TAS 120 can use the 4D image data from the learning stage to fill in any parts of the image that are missing when the TAS 120 later uses 2D slices during the tracking stage.

From the 4D image data, the TAS 120 can extract 2D slices (block 202) and perform 3D motion field estimation between times such as can serve as endpoints of a time frame (block 204). Referring first to the 3D motion field estimation (block 204), to quantify motion in the 4D image data 200, the TAS 120 can extract a first reference 3D image data volume. As 3D image data volumes are progressing in time, the changes between two image data volumes can be characterized as a deformation defined by a deformation vector field. The TAS 120 can perform 3D motion field estimation by, for example, calculating deformation vector fields (DVF) to find the deformation between each successive 3D image data volume and the reference 3D image data volume. In some examples, the deformation can be a pixel-to-pixel (or voxel-to-voxel) deformation in time where each pixel (or voxel) can have a deformation vector that defines its movement from one 3D image to the next 3D image, e.g., if a patient had a very small calcification the vector can define how that calcification moved. If there is no deformation, all pixel (or voxel) deformation vectors point are null. If there is deformation, the pixel (or voxel) deformation vectors point in various directions.

In an example, the processor circuit 126 of the TAS 120 can use a nonlinear registration technique to determine the deformation. In an example, the processor circuit 126 can calculate a DVF for each pixel (or voxel) in an image. In an example, the processor circuit 126 can calculate a DVF for pixels (or voxels) in an area of interest, e.g., specific to a target or organ at risk, such as of a segmented or other image. In some cases, for reduced computational complexity, the TAS 120 can use rigid registration instead of deformable registration.

After the TAS 120 calculates the DVFs, the TAS 120 has a set of DVFs that describe how the organ moves, e.g., translates and/or rotates, and/or deforms during respiration. The set of DVFs can include a substantial amount of information, which can be computationally difficult to process. To simply the computation, the processor circuit 126 of the TAS 120 can reduce the dimensionality of the set of DVFs, if desired.

First, the processor circuit 126 of the TAS 120 can apply a dimensionality reduction technique to the DVFs. As seen in FIG. 2, the dimensionality reduction technique can include applying a principal component analysis (PCA) to the 3D motion field data (block 206). Application of PCA to the DVFs results in a set of principal components or coefficients, which define vectors. Then, using a predefined criterion, such as a predefined amount of variability, or a predefined desired accuracy of a reconstructed deformation field, the TAS 120 can reduce the dimensionality by selecting one or more PCA components from the set of principal components (block 208). In an example, the accuracy can be defined as a measure of the difference between a reconstructed deformation field and the ones given by the registration.

Dimensionality reduction techniques are not limited to the use of PCA. Other non-limiting examples of dimensionality reduction techniques include independent component analysis (ICA), kernel PCA, canonical correlation analysis, locally linear embedding (LLE), Hessian LLE, Laplacian eigenmaps, local tangent space alignment, maximum variance unfolding, and maximally informative dimensions.

As indicated above, the TAS 120 can extract 2D slices from the 4D image data volume (block 202). As with the 3D image data volumes, the TAS 120 can perform 2D motion field estimation by, for example, calculating DVFs to find the deformation between successive 2D image data (2D slices)(block 210).

In some examples, the TAS 120 can select arbitrary slices within the 4D image data volume. In other examples, the TAS 120 can determine and select an orientation such as a plane, e.g., sagittal, axial, coronal, such as that having the most motion information and select slices from that plane or other orientation. The "plane" associated with a particular MRI slice need not be strictly planar, and may include some curvature, such as due to MRI distortion artifacts, or a slice that has been at least partially compensated for the MRI distortion. For example, the TAS 120 can train on three planes and determine which plane provides the better prediction of 3D motion. In some examples, the TAS 120 can select slices from planes in three orthogonal directions and calculate a DVF in each of those planes.

After the TAS 120 calculates the DVFs for the 2D image data, the TAS 120 has a set of DVFs. To simply the computation, the processor circuit 126 of the TAS 120 can reduce the dimensionality of the set of DVFs by applying a dimensionality reduction technique to the DVFs. The dimensionality reduction technique can include the TAS 120 applying a PCA to the 2D motion field data (block 212) to generate a set of principal components. Then, using a predefined criterion, such as a predefined amount of variability, or a predefined desired accuracy of a reconstructed deformation field, the TAS 120 can reduce the dimensionality by selecting one or more PCA components from the set of principal components (block 214).

For example, during the PCA analysis, the TAS 120 can determine the main components variation. By way of specific example, the $1^{st}$ principal component may be the largest and can explain 75% of variability and the $2^{nd}$ principal component can explain 10%. If a predefined amount of variability is 85%, then the TAS 120 can select the $1^{st}$ and the $2^{nd}$ principal components.

In an example, the accuracy can be defined as a measure of the difference between a reconstructed deformation field and the ones given by the registration.

After the TAS 120 has optionally reduced the dimensionality of both the 3D motion field PCA and the 2D motion field PCA, the processor 126 of the TAS 120 can generate a multivariate, multidimensional function $f$ that establishes a relation between, or links, the 2D PCA components and the 3D PCA components. The function $f$ can be, for example, a linear regression between a column Y that contains the 3D PCA components of the deformation vector fields, and a column X that contains the 2D PCA components, as shown below:

$$Y = \begin{pmatrix} y_{11} & \cdots & y_{1n} \\ \vdots & \ddots & \vdots \\ y_{m1} & \cdots & y_{mn} \end{pmatrix}$$

$$X = \begin{pmatrix} 1 & x_{11} & \cdots & x_{1p} \\ \vdots & \vdots & \ddots & \vdots \\ 1 & x_{m1} & \cdots & x_{mp} \end{pmatrix}$$

where $y_{ij}$ is the j coordinate in the principal component basis of the i time series in the 3D PCA, $x_{ij}$ is the j coordinate in the principal component basis of the i time series in the 2D PCA, m is the number of samples in the time series, n is the number of components for the 3D PCA, and p is the number of components for the 2D PCA for the slice under consideration.

The linear regression can be shown by the following:

$$\begin{pmatrix} y_{1j} \\ \vdots \\ y_{mj} \end{pmatrix} = \begin{pmatrix} 1 & x_{11} & \cdots & x_{1p} \\ \vdots & \vdots & \ddots & \vdots \\ 1 & x_{m1} & \cdots & x_{mp} \end{pmatrix} \begin{pmatrix} \beta_0 \\ \vdots \\ \beta_p \end{pmatrix}$$

where j is the coordinate of the j component in 3D PCA for all time series, and $\beta$ is a vector of the regression coefficient.

In some examples, the linear regression technique is principal component regression. Although a linear regression technique was described any type of regression analysis can be used, such as one or more non-linear regression techniques. The process is not restricted to linear regression, such as where $f$ is a multivariate, multidimensional function.

Once the TAS 120 has calculated the function $f$ (block 216), the TAS can calculate the model that links the 2D slices to the 3D motion (at block 218). The model can include the components of the 2D PCA and the 3D PCA and the function $f$ that links them.

During the tracking stage, the TAS 120 can obtain 2D slices in any orientation, e.g., sagittal, sagittal-axial, sagittal-axial-coronal, as long as the slices are in the same anatomical location as the one used during the learning stage. Then, the TAS 120 can calculate a PCA of the obtained image data and use the model to map the image data back to see what an estimate of full 3D motion should be.

In some examples, the model in the learning stage can be built from a set of 4D MRI data. In some such examples, the set of 4D MRI data can be obtained from a phase or amplitude-binned 4D MRI scan acquired at an earlier time, or just prior to treatment. Image data can be obtained over a plurality of respiratory cycles, where individual respiratory cycles include a plurality of portions, and the TAS 120 can generate at least two 3D image data volumes using a central tendency of the image data in like-portions. For example, the respiration cycle can be binned and the TAS 120 can generate a 3D image by taking information from the same bins at different respiratory phases. In this manner, the TAS 120 can generate a 4D image averaged over multiple respiratory cycles.

In other examples, the 4D MRI data can be obtained from a series of fast 3D MRI scans. In some cases, e.g., if 4D image data is not available, the 4D MRI data can be simulated from a static 3D MRI image, such as with some additional hypotheses, such as modeling the motion dynamics.

Figure 3:
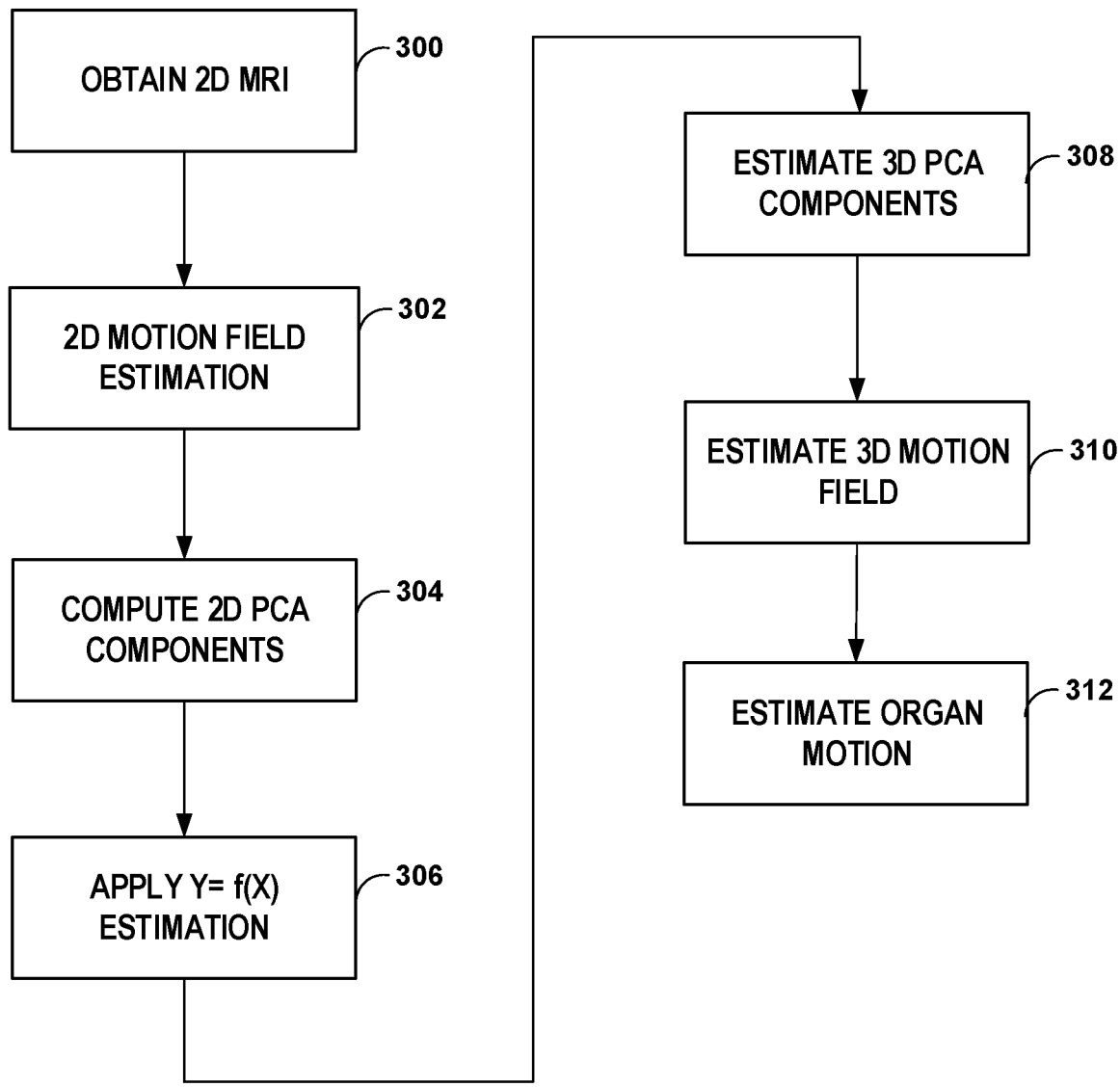
FIG. 3 is a flow diagram illustrating an example of a technique that can be used to estimate a real-time 3D image of a patient using the conversion model built according to the flow diagram of FIG. 2.

FIG. 3 is a flow diagram illustrating an example of a technique that can be used to estimate a real-time 3D image of a patient using the conversion model built according to the flow diagram of FIG. 2. The flow diagram of FIG. 3 represents the real-time tracking stage in which the TAS 120 can approximate a 3D motion field estimation, including applying the conversion model to the 2D motion field estimation, and determine at least one real-time change, e.g., 3D location, 3D deformation, and/or 3D rotation, of at least a portion of the target or region based on the approximated 3D motion field.

In FIG. 3, the TAS 120 can obtain a plurality of real-time image data corresponding to 2D images, e.g., 2D MRI slices (block 300). In some examples, the data images can include at least a portion of the target. The TAS 120 can perform 2D motion field estimation on the plurality of image data by, for example, estimating the real-time DVFs (and hence the real-time 3D image of the patient) to find the deformation between successive 2D image data, e.g., 2D slices, (block 302). Next, the TAS 120 can approximate 3D motion field estimation, which can include applying the conversion model to the 2D motion field estimation. For example, the TAS 120 can compute the 2D PCA of the newly obtained 2D image data, e.g., 2D slices, (block 304). Using the conversion model estimated by the function $f$ that links the 2D PCA and the 3D PCA (block 306), the TAS 120 can estimate the 3D PCA components (block 308). Using the estimated 3D PCA components, the TAS 120 can approximate a real-time 3D motion field estimation of a region of the patient (block 310), and thus estimate motion of a target, e.g., an organ at risk (block 312).

In some examples, the TAS 120 can determine the best orientation and position of 2D slices to image the patient during treatment. For example, the TAS 120 can determine a subspace containing the maximum information for each 3D PCA component. This subspace can contain deformation information that is the most correlated to the 3D image data volume and that provides give the most accurate prediction of motion. The TAS 120 can automatically select the best orientation for the choice of the 2D slice using this deformation information.

In some examples, the TAS 120 can enable real-time estimation of the 2D PCA components. For example, instead of computing a deformable registration between the 2D slices, the TAS 120 can perform an optimization process that can directly estimate the coordinates of the current slices in the 2D PCA, which will generate the best coordinates that deform the current slices to the model slice.

By determining the estimated motion of the target, the TAS 120 can control treatment by accurately gating the treatment if the at least a portion of the region is outside a predefined spatial gating window. In addition, the TAS 120 can control treatment by controlling an emitted radiation direction of a treatment delivery device to track the region.

It should be noted that although the techniques are described as subject-specific, the techniques of this disclosure can be extended to a general statistical 3D PCA. In that case, the 3D PCA determined during the learning stage can be determined on several subjects.

Before real-time tracking, it can be desirable for the TAS 120 to perform pre-alignment in a pre-processing stage to ensure that the originally acquired 4D image data from which the conversion model was determined is aligned to the patient's current position. It can be desirable to make sure that the slices used during the tracking stage are the same as was used during the learning stage. Misalignment can occur, for example, if the 4D image data was acquired on a previous day.

In the pre-alignment act, the TAS 120 can determine a correction for patient movement in between a first patient session at a first time, e.g., a learning stage on a first day, and a second patient session at a second time, e.g., a tracking stage on a second day. The TAS 120 can perform rigid alignment of the 3D PCA to the current patient. The TAS 120 can correct the 3D PCA components through various reorientation strategies, in the case of non-linear registration in the learning stage. In one example, the TAS 120 can determine which slices to use during the tracking stage based on the slices used during the modelling stage to ensure consistency.

Figure 4:
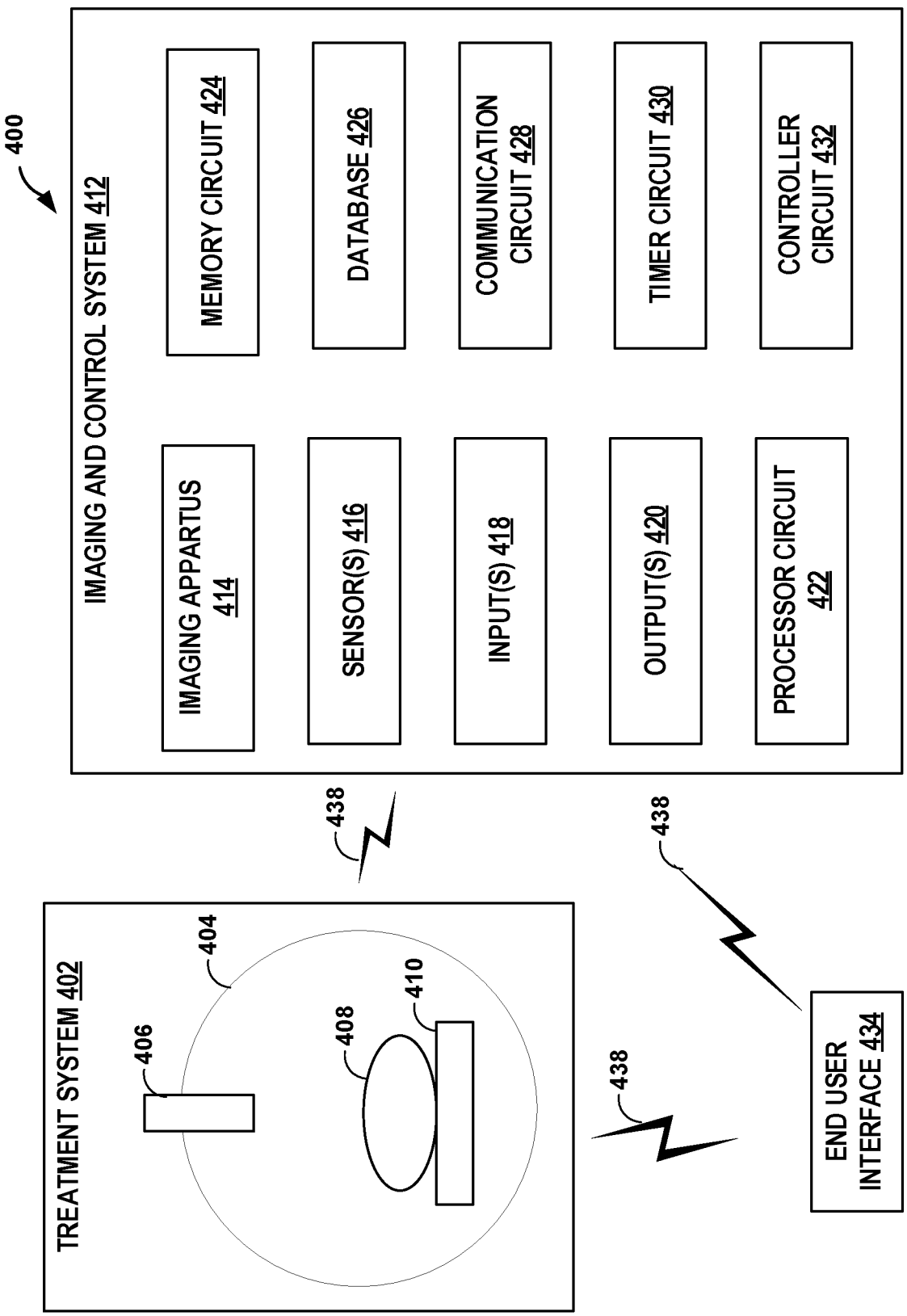
FIG. 4 illustrates an example of portions of a radiotherapy system.

FIG. 4 illustrates an example of portions of a radiotherapy system 400, e.g., MRI-guided LINAC. The radiotherapy system 400 can include a treatment system 402, an imaging system 412, and an end-user interface 434. The treatment system 402 can include a treatment apparatus, such as can include a linear accelerator ("linac"). The linac can be configured to deliver a radiotherapy treatment to a patient 408. The patient 408 can be positioned on a patient support 410, such as a table, a couch, or other surface. The patient support 410 can be configured to change position, such as relative to one or more other components of the linac, such as to elevate or change the longitudinal position of the patient 408. In an example, the patient support 410 can be configured to be motorized such that the patient 408 can be positioned with the target at or close to a center of the treatment apparatus.

Radiation can be emitted from a radiation source 406 toward the patient 408. In an example, the radiation source 406 can be configured to move, such as to rotate around the patient 408, such as by using a rotational support 404 (e.g., a gantry or a mechanical arm) to which the radiation source 406 can be attached. The radiation source 406 can be configured to direct an x-ray (or other particle) beam toward a target (e.g., a cancer tumor) of the patient 408. The radiation source 406 can be configured to rotate, such as to provide the patient 408 with a plurality of dosages of radiation (e.g., varying dosages), such as according to a treatment plan.

The imaging system 412 can include an imaging apparatus 414 such as a magnetic resonance imaging (MRI) machine that can be used with the treatment system 402 (e.g., such as to provide an MRI linear accelerator ("MRI-linac")). The MRI apparatus can be used to provide imaging information that can be used to determine a location of the target in the patient 408, such as to direct radiotherapy to a specified location of the patient 408, such as to the target. The imaging system 412 can additionally or alternatively include a computed tomography (CT) system, or another imaging system. The imaging system 412 can include one or more sensors 416. The one or more sensors 416 can include a flat panel detector (e.g., an X-ray detector), such as can be arranged opposite an X-ray source. The imaging system 412 can include one or more inputs 418, one or more outputs 420, a processor circuit 422, a memory circuit 424, a database 426, a communication circuit 428, a timer circuit 430, and a controller circuit 432.

The imaging system 412 can acquire, for example, a reference image (e.g., a treatment planning image) of the patient 408 with at least three dimensions (e.g., the 3D MR reference image or a 4D MR reference image). In an example, information about the 3D MR reference image can be acquired by the imaging system. The 3D MR reference image can be useful in determining a location of a region of interest of the patient (e.g., the target). In an example, during the treatment session of the patient 408, the imaging system 412 can acquire a plurality of one-dimensional (1D) lines, two-dimensional (2D) slice or projection images, a 3D MR image (e.g., a 3D image of a volume), or a 4D MR image (e.g., a sequence of 3D MR images over time).

The treatment system 402 can be communicatively coupled to the imaging system 412 and the end-user interface 434. The imaging system 412 can include or be communicatively coupled to the end-user interface 434. This communicative coupling can include using one or more communication links (e.g., communication link 438), such as can include a wired or wireless transmitter, receiver or transceiver circuits (such as at each end of the communication link), a communication bus, a communication network, or a computer network.

The processor circuit 422 can be configured to determine information about a location (e.g., a position) of the target in the patient 408. The output 420 can be configured to provide information, such as about the position of the target, such as to the treatment system 402, such as during a radiotherapy session of the patient 408. The end-user interface 434 can be used by a caregiver, for example, a radiation oncologist, a radiation dosimetrist, or a radiation therapist (e.g., a radiographer). In an example, the end-user interface 434 can include an audio/visual indicator (e.g., a monitor). The controller circuit 432 can be configured to control one or more aspects of the imaging system 412. In an example, the controller circuit 432 can control the use or operation of the gradient coils of the imaging apparatus 414, such as to specify an orientation of the real-time 2D MR image slice. The memory circuit 424 can provide information to the processor circuit 422, which can implement the techniques described herein in hardware or software, or a combination of both on a general-purpose computer. In an example, the processor circuit 422 can include graphical processing unit (GPU).

This document describes, among other things, applying a conversion model to a 2D target or OAR motion estimation to obtain an estimated 3D target or OAR motion estimation, one or more other techniques for 3D motion estimation can be used in combination with the techniques described herein. For example, one or more aspects of various techniques described in this disclosure can be combined with one or more of aspects described in the following U.S. patent applications, which are incorporated herein by reference in their entirety: 1) U.S. patent application Ser. No. 62/090,115, titled "MAGNETIC RESONANCE PROJECTION IMAGING," filed on Dec. 10, 2014 ;2) U.S. patent application Ser. No. 62/069,066, titled "REAL TIME ORGAN MOTION PREDICTION DUE TO BREATHING FOR MRI-LINAC," filed on Oct. 27, 2014 ; 3) U.S. patent application Ser. No. 62/089,482, titled "MAGNETIC RESONANCE IMAGING TARGET LOCALIZATION," filed on Dec. 9, 2014 ; and 4) U.S. patent application Ser. No. 62/069,145, titled "MRI-LINAC REAL-TIME IMAGE GUIDANCE TECHNIQUES," filed on Oct. 27, 2014 .

Additional Notes

Example 1 includes subject matter (such as a method, means for performing acts, machine readable medium (such as a computer-readable medium) including instructions that when performed by a machine cause the machine to performs acts, or an apparatus configured to perform) of controlling real-time image-guided adaptive radiation treatment of at least a portion of a region of a patient, the method comprising obtaining a plurality of real-time image data corresponding to 2-dimensional (2D) magnetic resonance imaging (MRI) images including at least a portion of the region; performing 2D motion field estimation on the plurality of image data; approximating a 3-dimensional (3D) motion field estimation, including applying a conversion model to the 2D motion field estimation; determining at least one real-time change of at least a portion of the region based on the approximated 3D motion field estimation; and controlling the treatment of at least a portion of the region using the determined at least one change.

In Example 2, the subject matter of Example 1 may optionally include, using the conversion model, wherein the conversion model is specified by: obtaining at least two 3D image data volumes during a first time frame, the at least two 3D image data volumes including at least a portion of the region; performing 3D motion field estimation on the at least two 3D image data volumes obtained during the first time frame; obtaining 2D image data corresponding to at least two 2D images during the first time frame, the 2D image data including at least a portion of the region; performing 2D motion field estimation on the 2D image data obtained during the first time frame; and determining the conversion model using the reduced 3D motion field and the 2D motion field.

In Example 3, the subject matter of Example 2 may optionally include, wherein at least one of performing 3D motion field estimation and performing 2D motion field estimation includes calculating a deformation vector field.

In Example 4, the subject matter of one or more of Examples 2 and 3 may optionally include, reducing a dimensionality of at least one of the estimated 3D motion field and the estimated 2D motion field.

In Example 5, the subject matter of Example 4, may optionally include, performing a principal component analysis to determine a plurality of principal components; and wherein reducing a dimensionality of at least one of the estimated 3D motion field and the estimated 2D motion field includes selecting at least one of the principal components based on a predefined criterion.

In Example 6, the subject matter of one or more of Examples 2-5 may optionally include, wherein determining the conversion model using the reduced 3D motion field and the 2D motion field includes performing a principal component regression.

In Example 7, the subject matter of one or more of Examples 1-6 may optionally include, wherein controlling the treatment comprises: gating the treatment if the at least a portion of the region is outside a predefined spatial gating window.

In Example 8, the subject matter of one or more of Examples 1-7 may optionally include, wherein controlling the treatment comprises: controlling an emitted radiation direction of a treatment delivery device to track the region.

In Example 9, the subject matter of one or more of Examples 1-8 may optionally include, determining a correction for patient movement in between a first patient session at a first time and a second patient session at a second time.

In Example 10, the subject matter of one or more of Examples 2-9 may optionally include, wherein obtaining at least two 3D image data volumes during a first time frame includes: obtaining image data over a plurality of respiratory cycles, wherein individual respiratory cycles include a plurality of portions; and generating the at least two 3D image data volumes using a central tendency of the image data in like-portions.

In Example 11, the subject matter of one or more of Examples 1-10 may optionally include, wherein the at least one real-time change includes at least one real-time 3D defamation.

In Example 12, the subject matter of one or more of Examples 1-11 may optionally include, wherein the at least one real-time change includes at least one real-time 3D location.

In Example 13, the subject matter of one or more of Examples 1-12 may optionally include, wherein the at least one real-time change includes at least one real-time 3D rotation.

Example 14 includes subject matter (such as a device, apparatus, system, or machine) for controlling real-time image-guided adaptive radiation treatment of at least a portion of a region of a patient, comprising: a treatment adaptation system configured to: obtain a plurality of real-time image data corresponding to 2-dimensional (2D) magnetic resonance imaging (MRI) images including at least a portion of the region; perform 2D motion field estimation on the plurality of image data; approximate a 3-dimensional (3D) motion field estimation, including applying a conversion model to the 2D motion field estimation; determine at least one real-time change of at least a portion of the region based on the approximated 3D motion field estimation; and a therapy controller circuit configured to: control the treatment of at least a portion of the region using the determined at least one change.

In Example 15, the subject matter of Example 14 may optionally include, wherein the treatment adaptation system is configured to: using the conversion model, wherein the conversion model is specified by: obtain at least two 3D image data volumes during a first time frame, the at least two 3D image data volumes including at least a portion of the region; perform 3D motion field estimation on the at least two 3D image data volumes obtained during the first time frame; obtain 2D image data corresponding to at least two 2D images during the first time frame, the 2D image data including at least a portion of the region; perform 2D motion field estimation on the 2D image data obtained during the first time frame; and determine the conversion model using the reduced 3D motion field and the 2D motion field.

In Example 16, the subject matter of Example 15 may optionally include, wherein at least one of performing 3D motion field estimation and performing 2D motion field estimation includes calculating a deformation vector field.

In Example 17, the subject matter of one or more of Examples 15 and 16 may optionally include, wherein the treatment adaptation system is configured to: reduce a dimensionality of at least one of the estimated 3D motion field and the estimated 2D motion field.

In Example 18, the subject matter of Example 17 may optionally include, wherein the treatment adaptation system is configured to: perform a principal component analysis to determine a plurality of principal components; and wherein the treatment adaptation system configured to reduce a dimensionality of at least one of the estimated 3D motion field and the estimated 2D motion field includes selecting at least one of the principal components based on a predefined criterion.

In Example 19, the subject matter of one or more of Examples 15-18 may optionally include, wherein the treatment adaptation system configured to determine the conversion model using the reduced 3D motion field and the 2D motion field includes performing a principal component regression.

In Example 20, the subject matter of one or more of Examples 14-19 may optionally include, wherein the therapy controller circuit configured to control the treatment is configured to: gate the treatment if the at least a portion of the region is outside a predefined spatial gating window.

In Example 21, the subject matter of one or more of Examples 14-20 may optionally include, wherein the therapy controller circuit configured to control the treatment is configured to: control an emitted radiation direction of a treatment delivery device to track the region.

In Example 22, the subject matter of one or more of Examples 14-21 may optionally include, wherein the treatment adaptation system is configured to: determine a correction for patient movement in between a first patient session at a first time and a second patient session at a second time.

In Example 23, the subject matter of one or more of Examples 15-22 may optionally include, wherein the treatment adaptation system configured to obtain at least two 3D image data volumes during a first time frame is configured to: obtain image data over a plurality of respiratory cycles, wherein individual respiratory cycles include a plurality of portions; and generate the at least two 3D image data volumes using a central tendency of the image data in like-portions.

In Example 24, the subject matter of one or more of Examples 14-23 may optionally include, wherein the at least one real-time change includes at least one real-time 3D defamation.

In Example 25, the subject matter of one or more of Examples 14-24 may optionally include, wherein the at least one real-time change includes at least one real-time 3D location.

In Example 26, the subject matter of one or more of Examples 14-25 may optionally include, wherein the at least one real-time change includes at least one real-time 3D rotation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method of controlling real-time image-guided adaptive radiation treatment of at least a portion of a region of a patient, the computer-implemented method comprising:
   obtaining or generating a conversion model specified at least by performing a first 3-dimensional (3D) motion field estimation on data corresponding to at least two 3D image data volumes obtained during a first time frame and by performing a first 2-dimensional (2D) motion field estimation on 2D image data obtained during the first time frame;
   obtaining a plurality of real-time image data corresponding to 2D magnetic resonance imaging (MRI) images including at least a portion of the region;
   performing a second 2D motion field estimation on the obtained plurality of real-time image data corresponding to the 2D MRI images;
   approximating a second 3D motion field estimation by at least applying the conversion model to the second 2D motion field estimation;
   determining at least one real-time change of at least a portion of the region based on the approximated second 3D motion field estimation; and
   controlling the treatment of at least a portion of the region using the determined at least one change.

2. The computer-implemented method of claim 1, wherein the conversion model is further specified by:
   obtaining the at least two 3D image data volumes during the first time frame, the at least two 3D image data volumes including the at least a portion of the region;
   obtaining 2D image data corresponding to at least two 2D images during the first time frame, the 2D image data including the at least a portion of the region; and
   determining the conversion model using a reduced 3D motion field generated by performing the first 3D motion field estimation and the 2D motion field generated by performing the first 2D motion field estimation.

3. The computer-implemented method of claim 1, comprising:
   reducing a dimensionality of at least one of an estimated 3D motion field generated by performing the first 3D motion field estimation and an estimated 2D motion field generated by performing the first 2D motion field estimation.

4. The computer-implemented method of claim 3, comprising:
   performing a principal component analysis to determine a plurality of principal components; and
   wherein reducing a dimensionality of at least one of the estimated 3D motion field and the estimated 2D motion field includes selecting at least one of the principal components based on a predefined criterion.

5. The computer-implemented method of claim 2, wherein determining the conversion model using the reduced 3D motion field and the 2D motion field includes performing a principal component regression.

6. The computer-implemented method of claim 2, wherein obtaining at least two 3D image data volumes during a first time frame includes:
   obtaining image data over a plurality of respiratory cycles, wherein individual respiratory cycles include a plurality of portions; and
   generating the at least two 3D image data volumes using a central tendency of the image data in like-portions.

7. The computer-implemented method of claim 1, wherein at least one of performing the first 3D motion field estimation and performing the first 2D motion field estimation includes calculating a deformation vector field.

8. The computer-implemented method of claim 1, wherein controlling the treatment comprises:
   gating the treatment if the at least a portion of the region is outside a predefined spatial gating window.

9. The computer-implemented method of claim 1, wherein controlling the treatment comprises:
   controlling an emitted radiation direction of a treatment delivery device to track the region.

10. The computer-implemented method of claim 1, comprising:
    determining a correction for patient movement in between a first patient session at a first time and a second patient session at a second time.

11. The computer-implemented method of claim 1, wherein the at least one real-time change includes at least one real-time 3D defamation.

12. The computer-implemented method of claim 1, wherein the at least one real-time change includes at least one real-time 3D location.

13. The computer-implemented method of claim 1, wherein the at least one real-time change includes at least one real-time 3D rotation.

14. A system for controlling real-time image-guided adaptive radiation treatment of at least a portion of a region of a patient, the system comprising:
   a treatment adaptation system configured to:
      obtain or generate a conversion model specified at least by performing a first 3-dimensional (3D) motion field estimation on data corresponding to at least two 3D image data volumes obtained during a first time frame and by performing a first 2-dimensional (2D)

motion field estimation on 2D image data obtained during the first time frame;

obtain a plurality of real-time image data corresponding to 2D magnetic resonance imaging (MRI) images including at least a portion of the region;

perform a second 2D motion field estimation on the obtained plurality of real-time image data corresponding to the 2D MRI images;

approximate a second 3D motion field estimation by at least applying the conversion model to the second 2D motion field estimation; and determine at least one real-time change of at least a portion of the region based on the approximated second 3D motion field estimation.

15. The system of claim 14,
wherein the conversion model is further specified by:
obtaining at least two 3D image data volumes during the first time frame, the at least two 3D image data volumes including at least a portion of the region;
obtaining 2D image data corresponding to at least two 2D images during the first time frame, the 2D image data including at least a portion of the region; and
determining the conversion model using the reduced 3D motion field generated by performing the first 3D motion field estimation and the 2D motion field generated by performing the first 2D motion field estimation.

16. The system of claim 15, wherein the treatment adaptation system is configured to:
reduce a dimensionality of at least one of an estimated 3D motion field generated by performing the first 3D motion field estimation and the estimated 2D motion field generated by performing the first 2D motion field estimation.

17. The system of claim 16, wherein the treatment adaptation system is configured to:
perform a principal component analysis to determine a plurality of principal components; and
wherein the treatment adaptation system configured to reduce a dimensionality of at least one of the estimated 3D motion field and the estimated 2D motion field includes is configured to select at least one of the principal components based on a predefined criterion.

18. The system of claim 15, wherein the treatment adaptation system configured to determine the conversion model using the reduced 3D motion field and the 2D motion field includes performing a principal component regression.

19. The system of claim 15, wherein the treatment adaptation system configured to obtain at least two 3D image data volumes during a first time frame is configured to:
obtain image data over a plurality of respiratory cycles, wherein individual respiratory cycles include a plurality of portions; and
generate the at least two 3D image data volumes using a central tendency of the image data in like-portions.

20. The system of claim 14, wherein at least one of performing the first 3D motion field estimation and performing the first 2D motion field estimation includes calculating a deformation vector field.

21. The system of claim 14, wherein the therapy controller circuit configured to control the treatment is configured to:
gate the treatment if the at least a portion of the region is outside a predefined spatial gating window.

22. The system of claim 14, wherein the therapy controller circuit configured to control the treatment is configured to:
control an emitted radiation direction of a treatment delivery device to track the region.

23. The system of claim 14, wherein the treatment adaptation system is configured to:
determine a correction for patient movement in between a first patient session at a first time and a second patient session at a second time.

24. The system of claim 14, wherein the at least one real-time change includes at least one real-time 3D defamation.

25. The system of claim 14, wherein the at least one real-time change includes at least one real-time 3D location.

26. The system of claim 14, wherein the at least one real-time change includes at least one real-time 3D rotation.

27. The system of claim 14, further comprising:
a therapy controller circuit configured to:
control the treatment of at least a portion of the region using the determined at least one change.

* * * * *